United States Patent
Richards-Kortum et al.

(10) Patent No.: US 10,314,990 B2
(45) Date of Patent: Jun. 11, 2019

(54) BUBBLE CONTINUOUS POSITIVE AIRWAY PRESSURE

(71) Applicant: WILLIAM MARSH RICE UNIVERSITY, Houston, TX (US)

(72) Inventors: Rebecca Richards-Kortum, Houston, TX (US); Z. Maria Oden, Houston, TX (US); Jocelyn Kaye Brown, Pittsburgh, PA (US); Robert H. J. Miros, San Rafael, CA (US); Elizabeth Molyneux, Blantyre (MW)

(73) Assignee: William Marsh Rice University, Houston, TX (US)

( * ) Notice: Subject to any disclaimer, the term of this patent is extended or adjusted under 35 U.S.C. 154(b) by 586 days.

(21) Appl. No.: 14/722,393

(22) Filed: May 27, 2015

(65) Prior Publication Data
US 2015/0258291 A1   Sep. 17, 2015

Related U.S. Application Data

(63) Continuation of application No. PCT/US2013/071965, filed on Nov. 26, 2013.
(Continued)

(51) Int. Cl.
*A61M 16/00* (2006.01)
*A61M 16/12* (2006.01)
(Continued)

(52) U.S. Cl.
CPC .......... *A61M 16/0066* (2013.01); *A42B 1/02* (2013.01); *A61M 16/0003* (2014.02);
(Continued)

(58) Field of Classification Search
CPC .......... A61M 16/0066; A61M 16/0003; A61M 16/0672; A61M 16/0683; A61M 16/0816;
(Continued)

(56) References Cited

U.S. PATENT DOCUMENTS

| | | | | | |
|---|---|---|---|---|---|
| 4,011,866 | A | * | 3/1977 | Klein ............. | A61M 16/021 128/204.21 |
| 4,120,300 | A | * | 10/1978 | Tiep ............... | A61M 16/10 128/204.24 |

(Continued)

FOREIGN PATENT DOCUMENTS

WO    2012156885    11/2012

OTHER PUBLICATIONS

"Neonatal Nasal Bubble CPAP™ Fisher & Paykel Healthcare's F&P 850™ System" published Dec. 2, 2011, YouTube video: https://youtu.be/rMNGsI5RB5Q, by babysdocnicu.*

*Primary Examiner* — Andrew S Lo
(74) *Attorney, Agent, or Firm* — Robert R. Riddle; Matthew S. Gibson; Reed Smith LLP (57) ABSTRACT

A bubble continuous positive airway pressure system may include an adjustable flow generator configured to control a flow rate of air to be delivered to a patient. A pressure-regulated delivery system is configured to control a pressure delivered to the patient interface. The delivery system is operatively connected to a pressure control tube. One end of the pressure control tube is submerged in a liquid. A patient interface is configured to transfer pressure from the pressure control tube to the patient's airway.

4 Claims, 9 Drawing Sheets

Related U.S. Application Data (60) Provisional application No. 61/730,353, filed on Nov. 27, 2012.

(51) Int. Cl.
*A61M 16/20* (2006.01)
*A61M 16/06* (2006.01)
*A42B 1/02* (2006.01)
*A61M 16/08* (2006.01)

(52) U.S. Cl.
CPC .... *A61M 16/0672* (2014.02); *A61M 16/0683* (2013.01); *A61M 16/0816* (2013.01); *A61M 16/12* (2013.01); *A61M 16/20* (2013.01); *A61M 2016/003* (2013.01); *A61M 2202/0208* (2013.01); *A61M 2205/3334* (2013.01); *A61M 2205/3348* (2013.01); *A61M 2240/00* (2013.01)

(58) Field of Classification Search
CPC .................. A61M 16/12; A61M 16/20; A61M 2016/003; A61M 2202/0208; A61M 2205/3334; A61M 2240/00; A61M 16/0666; A61M 16/0858; A61M 16/1065; A61M 2205/3348; A42B 1/02
USPC .................................................. 128/201.22
See application file for complete search history.

(56) References Cited

U.S. PATENT DOCUMENTS

| | | | | |
|---|---|---|---|---|
| 4,151,843 A | * | 5/1979 | Brekke | A61M 16/0666 128/204.24 |
| D257,449 S | * | 10/1980 | Johnson, Jr. | D2/889 |
| 4,407,279 A | * | 10/1983 | Tschernezky | A61M 15/00 128/200.11 |
| 4,774,946 A | * | 10/1988 | Ackerman | A61M 16/0666 104/179 |
| 5,239,995 A | * | 8/1993 | Estes | A61M 16/024 128/204.18 |
| 5,388,571 A | * | 2/1995 | Roberts | A61M 16/16 128/200.18 |
| 6,332,462 B1 | * | 12/2001 | Krohn | A61M 16/1075 128/204.15 |
| 6,805,120 B1 | * | 10/2004 | Jeffrey | A61M 16/0096 128/204.17 |
| 6,889,689 B1 | | 5/2005 | Neuman | |
| 7,578,294 B2 | * | 8/2009 | Pierro | A61M 16/0666 128/204.18 |
| 8,020,551 B2 | * | 9/2011 | Virr | A61M 16/00 122/4 R |
| 2003/0047185 A1 | * | 3/2003 | Olsen | A61M 16/06 128/203.22 |
| 2005/0072470 A1 | * | 4/2005 | Jacobs | A61M 16/0666 137/251.1 |
| 2007/0283957 A1 | | 12/2007 | Schobel et al. | |
| 2009/0056719 A1 | * | 3/2009 | Newman, Jr. | A61M 16/0666 128/204.18 |
| 2009/0194108 A1 | * | 8/2009 | Newman, Jr. | A61M 16/0666 128/204.18 |
| 2010/0147302 A1 | | 6/2010 | Selvarajan et al. | |
| 2010/0154796 A1 | * | 6/2010 | Smith | A61M 16/16 128/203.26 |
| 2010/0326442 A1 | | 12/2010 | Hamilton et al. | |
| 2011/0073112 A1 | | 3/2011 | Diblasi et al. | |
| 2011/0079222 A1 | * | 4/2011 | DiBlasi | A61M 16/021 128/203.12 |
| 2012/0012112 A1 | | 1/2012 | Dunsmore et al. | |
| 2015/0075524 A1 | * | 3/2015 | Millar | A61M 16/105 128/202.27 |
| 2015/0128941 A1 | * | 5/2015 | Holley | A61M 16/0051 128/203.14 |

\* cited by examiner

BUBBLE CONTINUOUS POSITIVE AIRWAY PRESSURE

CROSS-REFERENCE TO RELATED APPLICATION

This application is Continuation of International Application No. PCT/US13/71965, filed Nov. 26, 2013, which was published as International Publication No. WO 201485431, which claims the benefit of U.S. Provisional Application No. 61/730,353, filed Nov. 27, 2012 entitled "BUBBLE CONTINUOUS POSITIVE AIRWAY PRESSURE," the disclosure of which is incorporated herein by reference in its entirety.

STATEMENT OF GOVERNMENT INTEREST

This invention was made with government support under Grant No. AID-OAA-G-11-00065 awarded by the USAID. The government has certain rights in the invention.

BACKGROUND

Acute respiratory infections are the leading cause of global child mortality. There is an important need for new, cost-effective technologies to treat infants and small children with respiratory distress. This need is most acute in the hours after birth. 20-38% of deaths in the first 48 hours of life are attributed to respiratory failure. Moreover, complications associated with premature birth, often related to breathing problems, are responsible for an additional 30% of neonatal mortality.

SUMMARY

The present disclosure generally relates generally to bulb continuous positive airway pressure ("bCPAP") systems, devices, and methods to provide simple, low-cost respiratory support for patients. The systems, devices and methods of the present disclosure provide the same therapeutic flow and pressure as systems used in high-resource settings.

Intended users of the systems, devices and methods of the present disclosure are healthcare providers in developing hospitals. A primary patient group is infants under one year of age who suffer from various respiratory conditions, which include underdeveloped lungs and respiratory infections. The systems, devices and methods of the present disclosure require minimal training, which may be provided by educational materials. In the future, the systems, devices and methods of the present disclosure may also be used in developed countries, as the cost is significantly less than that of currently available bubble CPAP systems.

The features and advantages of the present disclosure will be apparent to those skilled in the art. While numerous changes may be made by those skilled in the art, such changes are within the spirit of the invention.

DRAWINGS

Some specific example embodiments of the disclosure may be understood by referring, in part, to the following description and the accompanying drawings.

FIG. 1 is a block diagram and FIG. 2 is a perspective view of a bCPAP system according to one embodiment of the present disclosure. The system includes an adjustable flow generator, a pressure-regulated delivery system, and, a patient interface. Flow may be generated by two or more air pumps that can be blended with oxygen from a tank or concentrator. The total flow rate and fraction of oxygen delivered are controlled by two or more flow regulators. The output of the flow generator is connected to the pressure-regulated delivery system. Pressure may be controlled by submerging a pressure control tube in a column of water. The mean pressure in the system may be determined by the height of the water column. The patient interface is also connected to a pressure control tube, ensuring that the pressure in the patient interface and the pressure control tube are at least generally, if not exactly, equivalent. The pressurized air mix is delivered to the patient's nostrils via a set of binasal prongs terminated at the distal end.

FIG. 7A displays a reference standard bCPAP device used clinically in the US and FIG. 7B displays a low-cost bCPAP device according to one embodiment of the present disclosure. Dotted lines show the mean and average peak pressures, averaged across 60 seconds of data collection. The pressure waveforms of the two devices are similar, indicating delivery of equivalent therapeutic pressure. In both devices, the mean pressure is controlled by adjusting the height of water in the pressure control tube, and the high frequency oscillations about the mean are associated with the formation of bubbles at the distal tip of the pressure control tube. There were no statistically significant differences between the pressures generated by the two devices (Student t-test, $p<0.01$).

DETAILED DESCRIPTION

The present disclosure generally relates to bulb continuous positive airway pressure systems, devices, and methods. Certain terminology is used in the following description for convenience only and is not limited. Unless specifically set forth herein, the terms "a," "an" and "the" are not limited to one element, but instead should be read as "at least one."

The bubble CPAP (bCPAP) system, generally designated 100, of the present disclosure, according to certain embodiments, may have the following traits: (1) adjustable flow rates, (2) an ability to mix oxygen into the flow stream; (3) a mechanism to control the pressure delivered to the patient; (4) a low cost to manufacture; (5) are safe; (6) are durable; and/or (7) are easy to use and repair.

The bCPAP device 100 of the present disclosure delivers a source of continuous pressurized room (ambient) air, which can be supplemented with oxygen from an oxygen source 96 (see FIG. 1), such as a concentrator or cylinder, if desired or required. The device 100 is capable of delivering a mixture of pressurized air and oxygen at flow rates ranging from 0-10 liters per minute, pressures varying from 5-8 cm $H_2O$, and oxygen ranging from 21-65%. The oxygen in the oxygen source 96 may be pure or substantially pure oxygen. The oxygen source 96 may be capable of supplying oxygen at 10 liters per minute. The blended, pressurized flow is delivered to the patient's nostrils via nasal prongs 11.

Figure 1:
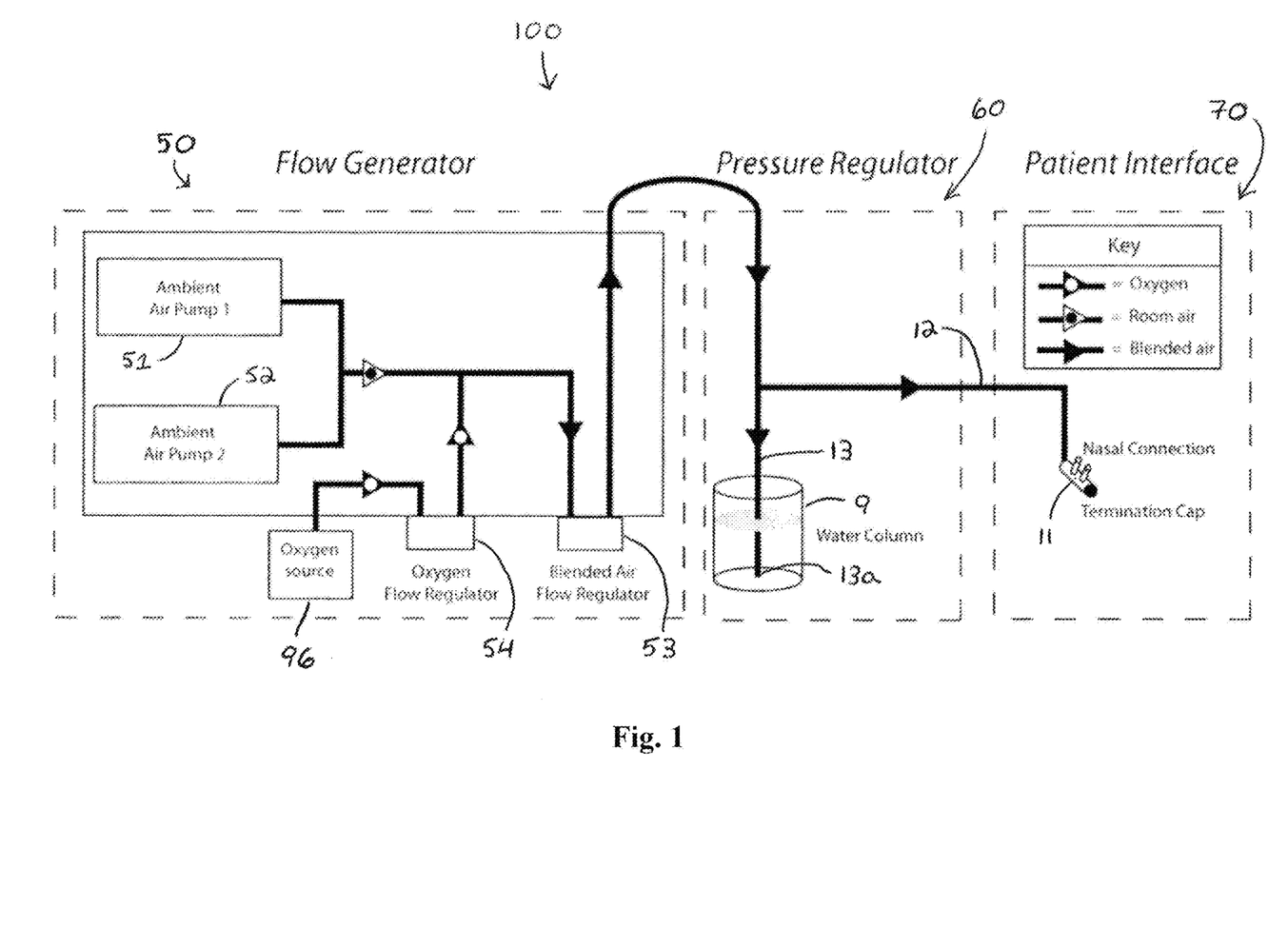
Figure 2:
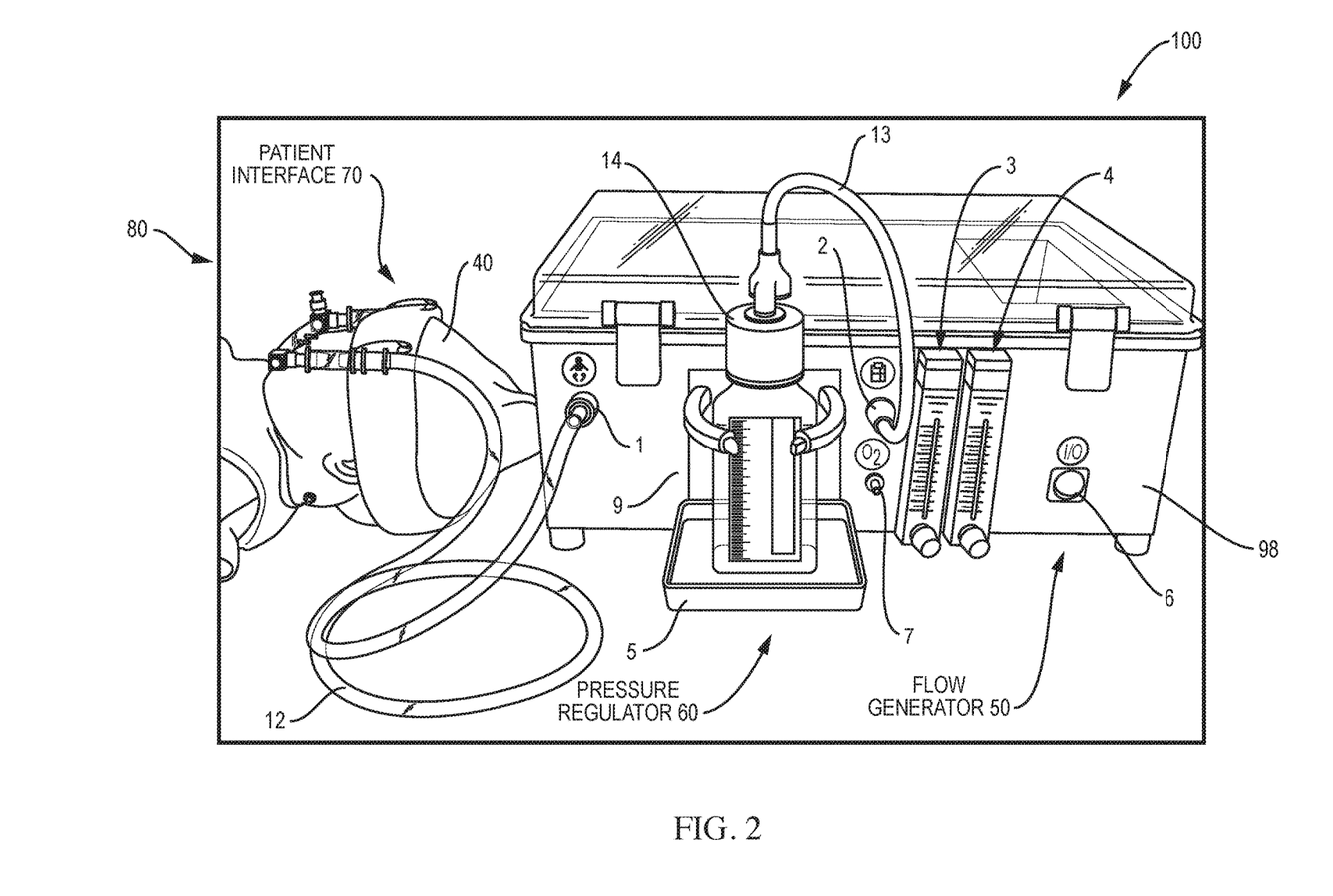

Referring to FIGS. 1 and 2, the device 100 may include three primary sub-systems: an adjustable flow generator 50, a pressure-regulated delivery system or pressure regulator 60, and a patient interface 70. The flow generator 50 controls the flow rate and the mix of oxygen and air delivered to the patient 80, such as a newborn or infant. The delivery system 60 controls the pressure delivered to the patient interface 70. The adjustable flow generator 50 and pressure-regulated delivery system 60 may be placed next to the patient's bed, as shown in FIG. 2.

The adjustable flow generator 50 may include two diaphragm pumps 51, 52 that are used to provide a continuous flow of room (ambient) air through a 0.25" inner diameter vinyl tubing to a standard flow regulator 53, which can be adjusted to set the total flow rate provided to the delivery system 60. The diaphragm pumps 51, 52 may be commercially available and may each output up to 16 L/min of flow. Alternatively, flow may be generated by a nebulizer or air mattress pumps. If required, the oxygen source 96 can be connected to an input port 7 in the flow generator 50 via an elongated oxygen tube 10. A second standard flow regulator 54 may be used to adjust the proportion of oxygen blended with room air. A look-up table on an exterior or a cover 98 of the device 100 allows the user to quickly adjust the oxygen flow rate to the desired percentage of oxygen concentration for a given total flow rate.

The pressure-regulated delivery system 60 can control the pressure at which the blended air mix is delivered to the patient 80 via the patient interface 70. The output of the flow generator 50 enters the pressure-regulated delivery system 60 where it is connected in parallel to a pressure control or bottle tube 13 and the patient interface 70. As shown in FIG. 1, a distal tip 13a of the pressure control tube 13 may be submerged in a bottle or column 9 of liquid, such as water. The depth of water in the bottle 9 may control or determine the pressure in the delivery system 60 and, therefore, the pressure delivered to the patient's airway and lungs to keep them inflated. The water bottle 9 acts as a pressure relief valve; bubbles form as pressure in the system exceeds that set by the height of the water column 9.

The patient interface 70 is designed to transfer pressure from the pressure control tube 13 to the patient's airway. The pressurized air mixture is delivered to at least one or both of the patient's nostrils via a set of binasal prongs 11, which are terminated at a distal end thereof with a short section of sealed tubing (see FIGS. 2, 4 and 5). An elongated patient tube 12 may operatively connect to prongs 11 to the delivery system 50. The prongs 11 may be binasal prongs made from cut nasal cannula that insert into the infant's nares. The patient tube 12 may be a smooth vinyl tube. The prongs 11 may be attached to a stockinette hat 40 with one or more safety pins 41 and elastic bands 42. This method of attachment holds the prongs 11 securely in place, even when the baby 80 moves, without adhesives, which could damage a baby's delicate skin.

The following description explains a method of administering the bCPAP system according to one embodiment of the present disclosure. Those skilled in the art understand that the following steps may be administered or performed in a modified or, in some cases, a reverse order, as desired, without reducing the effectiveness of the procedure.

Initially, the bottle 9 is filled with a liquid, such as fresh water (between 5-8 cm, according to doctor's orders), and a lid 14 is attached to the bottle 9. To increase pressure, water may be added to the bottle 9 with a syringe. To decrease pressure, water may be removed from the bottle 9 with a syringe. Next, the bottle 9 may be placed into a bottle holder 5 of the device 100 and a first end of the bottle tube 13 may be connected to the bCPAP device 100 at the bottle tubing port 2 and an opposing second end of the bottle tub 13 may be connected to the lid 14 of the bottle 9.

An appropriate prong size should be chosen for the patient interface 70. It is preferred that prongs 11 of varying size are available. The appropriate prong size may be based on the patient's weight. For infants at the high end of any of the weight ranges, it is prudent to consider using prongs for the next higher weight range. The prong size may be located between the nasal prongs.

Figure 4:
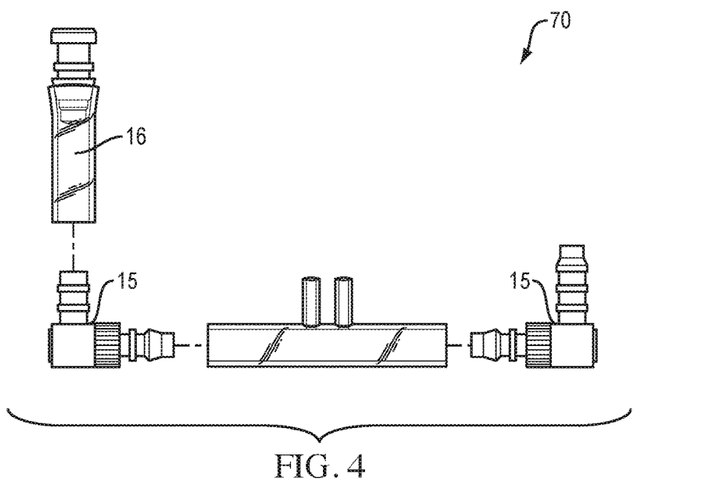
FIG. 4 is a top plan view of a partially disassembled patient interface according to one embodiment of the present disclosure.
Figure 5:
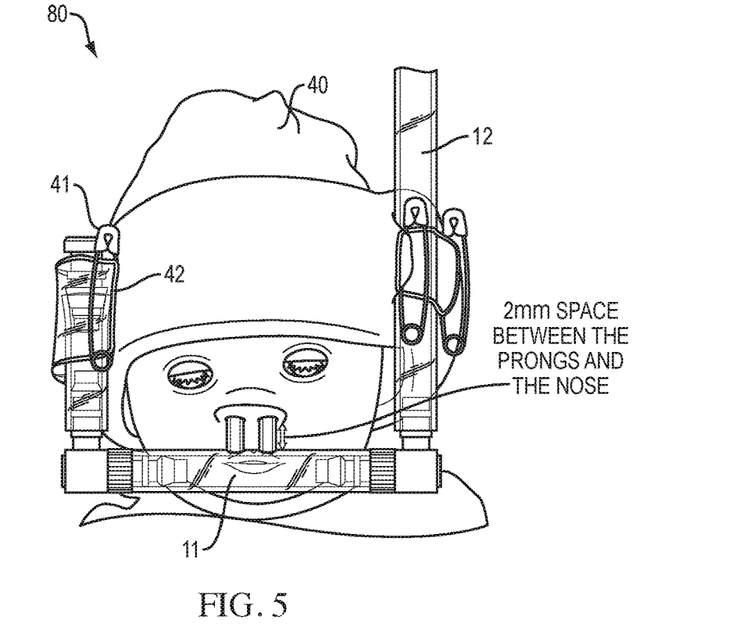
FIG. 5 is a top plan view of the patient interface and a patient tube attached to a patient.

The patient interface 70 may be pre-assembled or formed as an integral and unitary structure. However, it may be necessary to assembly the patient interface prior to administering the treatment. In such an embodiment, it is important to make sure that two elbow connectors 15 and a straight connector 16 are properly attached, as shown in FIGS. 4 and 5. Scissors and adhesive, such as glue or tap, may add the user in construction of the patient interface 70. Any prong size can be used within the same elbow and straight connectors 15, 16.

The prong size should be checked prior to administering the treatment. The prong size may be checked by placing the prongs 11 at least partially into the patient's nostrils. The prongs 11 should be placed curved-side down, so that the arucate shape of the prongs 11 points toward the patient 80. The prongs 11 should completely fill each nostril, and then the prongs 11 should be removed from the nostrils immediately. If the nostrils are not completely filled, air will leak and the patient 80 will not get the necessary pressure. In such a case, replace the prongs 11 with the next largest prong size.

Once the prong size is determined, a first end of the patient tube 12 may be connected to the bCPAP machine 100 at the patient tubing port 1. An opposing second end of the patient tube 12 can then be connected to the patient interface 70. In particular, the second end of the patient tube 12 may be connected to one end of one of the two elbow connectors 15 (see FIG. 5). It is important to not insert the prongs 11 into the patient 80 at this step.

Next, connect a first end of the power cord 8 to the back of the bCPAP machine 100 and an opposing second end of the power cord 8 to an electrical outlet. The bCPAP machine 100 may only operate on AC power. When a power switch 6 of the bCPAP machine 100 is engaged or turn "on," an indicator, such as a red light, may be activated or lit.

If the patient 80 needs oxygen, the oxygen concentrator 96 should be turned "on." Previously or subsequently, tubing 10 should be used to attach the oxygen concentrator 96 to the $O_2$ port 7 of the bCPAP machine 100.

If the patient does not need oxygen, the oxygen connector 96 should not be turned "on" or connected to. In addition, an oxygen flow meter 3 of the bCPAP machine 100 may be closed or turned "off."

Most CPAP patients start at the same settings, as provided in Table 1 below:

TABLE 1.

Standard Settings

|  | Total Flow | Oxygen Flow |
|---|---|---|
| Neonate | 6 L/min | 3 L/min |
| Child | 6 L/min | 4 L/min |

Figure 3:
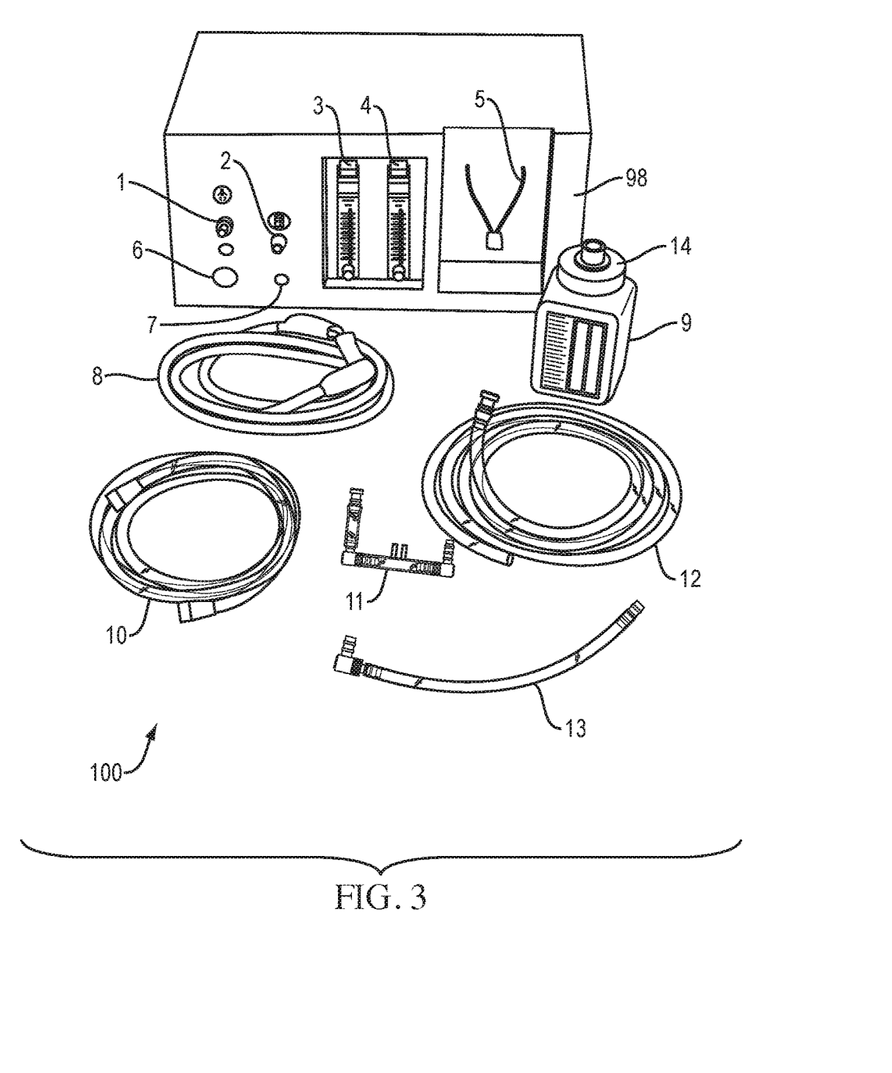
FIG. 3 is a perspective view of a partially disassembled bCPAP system according to another embodiment of the present disclosure.

As shown in FIGS. 2 and 3, the bCPAP machine 100 includes an oxygen flow meter 3 and a total flow meter 4 on an exterior therefore. The oxygen flow meter 3 should be set by the user or healthcare provider prior to setting a total flow meter 4 to the chosen settings. If a specific fraction of inspired oxygen ($FiO_2$) is required, the oxygen flow and the total flow can be determined based on tables leading to the value.

Checking the bubbling function prior to administering the treatment may be prudent to ensure proper deployment. To do so, cover the prongs 11 so as to prevent air flow in or out of the prongs 11. The prongs 11 may be covered by pinching the prongs 11 between the index finger and thumb, for example. If the system is functioning properly, water in the bottle 9 should bubble. When the prongs 11 are opened, the bubbling in the bottle 9 should stop. If the bubbling does not start or stop as described above, there is likely a problem with the system that should be addressed prior to administering the treatment. One common problem is that the bottle tube 13 and/or the patient tube 12 are not correctly connected. Alternatively, the total flow may be at least slightly increased until the water starts to bubble. The bCPAP device 100 may include a safety alarm that detects when bubbling stops or decreases. The safety alarm may also sound or illuminate if power is lost to the bCPAP device 100.

The system of the present disclosure may be administered by placing the hat 40 on the patient's head as part of or combined with the patient interface 70. The hat 40 may be pre-formed or manufactured, or the hat 40 may be assembled shortly before administering the treatment. In the latter embodiment, the hat size is based on the size of the patient's head using Table 2 below:

TABLE 2

Forming the Hat

| Hat Size | Stockinette Length | Stockinette Width |
|---|---|---|
| Small | 61 cm (24 in) | 2 inch |
| Medium | 66 cm (26 in) | 3 inch |
| Large | 71 cm (28 in) | 4 inch |

Figure 6A:
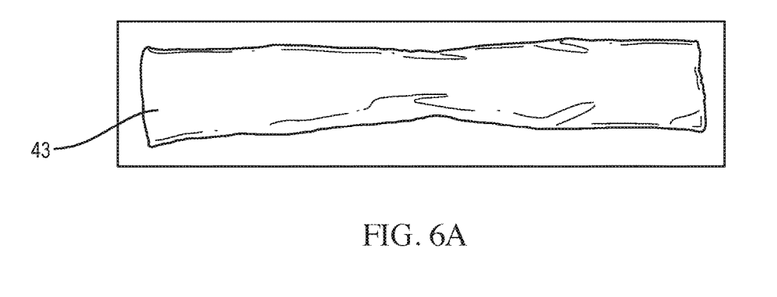
FIG. 6A is a top plan view of a stockinette used to form a hat according to one embodiment of the present disclosure.
Figure 6B:
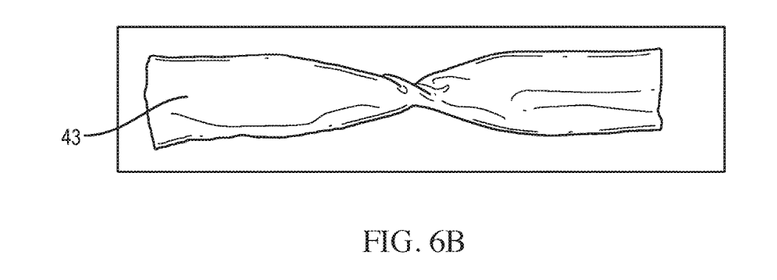
FIG. 6B is a top plan view of the stockinette in a partially twisted state.
Figure 6C:
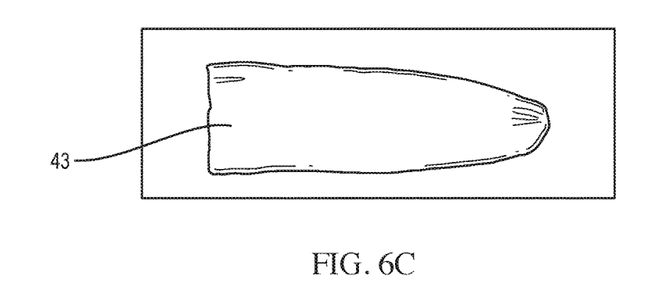
FIG. 6C is a top plan view of the partially twisted stockinette in a folded configuration.
Figure 6D:
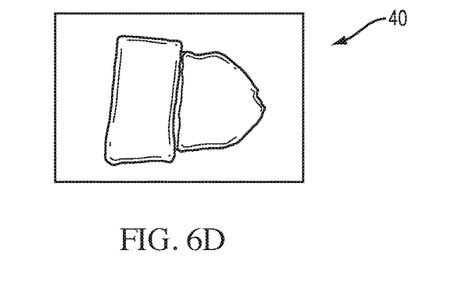
FIG. 6D is a top plan view of the hat.

Referring to FIG. 6A, once the hat size is determined, a stockinette 43 may be measured to the appropriate length and cut accordingly. The stockinette 43 may then be twisted in the middle, as shown in FIG. 6B. Next, one half of the stockinette 43 may be pulled over the other half, as shown in FIG. 6C. The bottom edge of the stockinette 43 may then be folded three times to make a 5-cm brim, as shown in FIG. 6D.

Prior to administering the treatment, the hat 40 may be placed on the patient's head. The hat 40 should fit tightly to prevent the prongs 11 from inadvertently moving with respect to the patient's head. The back of the hat 40 should be low, near the baby's neck. The hat 40 may need to be replaced at least every twenty four hours to keep a tight fit on the baby's head.

When the above has been accomplished and treatment is ready to be administered, it is important to remember to turn the bCPAP machine 100 "on." Saline drops may be inserted into the patient's nose to facilitate treatment. The prongs 11 may then be placing into the nose such that there is a 2 mm space between the prongs 11 and the nose (see FIG. 5). It is important not to use creams or ointments, as these can cause breakdown of the tissue and block the prongs 11. If power is lost during treatment, remove the prongs 11 from the patient's nostrils immediately. Then, place the patient 80 on oxygen. If possible, the bCPAP machine 100 should be taken to a ward with power. Also, record how long the patient was off of the bCPAP machine 100.

The bCPAP device 100 is a considerable improvement over existing methods in terms of cost. Conventional CPAP machines can cost, on average, over $6000. The startup cost of the bCPAP device 100 of the present disclosure, may be less than $200. Subsequent costs for additional tubing and patient interfaces may be less than $5 per patient. The bCPAP device 100 is also designed to be easy to manufacture and use, power-efficient, sterilizable, and culturally acceptable.

The bCPAP device 100 may be provided with a kit including a teaching module, a user manual and/or a repair manual. The module and manuals may detail diseases and conditions requiring bubble CPAP use, how to operate the device 100, potential problems, and/or repair instructions. For example, the repair manual may detail the procedure necessary to identify a defective pump 51, 52, obtain access to the pumps 51, 52, repair any defective components, and/or reassemble the device 100. The teaching manual may detail how to create the hat 40 and/or attach the patient interface 70 to the hat 40. The teaching manual may also describe characteristics of the patient that should be observed and noted during therapy to ensure a safe and effective procedure. The user manual may detail how to set-up and operate the device 100, for example.

To facilitate a better understanding of the present disclosure, the following examples of certain aspects of some embodiments are given. In no way should the following examples be read to limit, or define, the entire scope of the invention.

EXAMPLES

The following describes the technical performance of the present device and compares it to that of a reference standard bubble CPAP device. Two case reports are presented that illustrate the use of the low-cost bCPAP device to successfully treat a child with respiratory distress and a neonate with respiratory distress due to congenital pneumonia in a low-resource setting.

Pressure Testing Methodology: Pressure delivered by the bCPAP system was measured by blocking the outflow from the binasal prongs and connecting a pressure transducer (Model PX137-001DV, Omega Engineering, Inc.) just distal to the prongs. The device was set to deliver room air and prong pressure was measured for 60 seconds; data were collected at flow rates of 4, 6, 7, and 8 L/min and with the pressure control tube submerged in 4 and 6 cm of $H_2O$. The bCPAP system was disassembled and reassembled, and the testing process was repeated 10 times. The average pressure was calculated; in addition, pressure minima and maxima were detected and the average peak pressures were calculated. As a reference standard, nasal prong pressures were obtained under the same conditions for a clinical bCPAP system used therapeutically at Texas Children's Hospital. Wall air was used as an adjustable flow generator, and an Airlife Infant heated wire circuit was used to deliver flow to the prongs and a pressure control system. Data from the two systems were compared for the same flow and pressure settings.

Clinical Study: As part of a clinical study to evaluate the therapeutic performance of the bCPAP system at Queen Elizabeth Central Hospital, the device was used to treat a 6-month old child with bronchiolitis and a neonate with respiratory distress due to congenital pneumonia. Oxygen saturation, respiratory rate, work of breathing, and heart rate were monitored immediately before and after initiating therapy and then twice daily thereafter. Nasal saline drops were given every four hours during the duration of bCPAP therapy to prevent mucosal drying.

Results

Figure 7A:
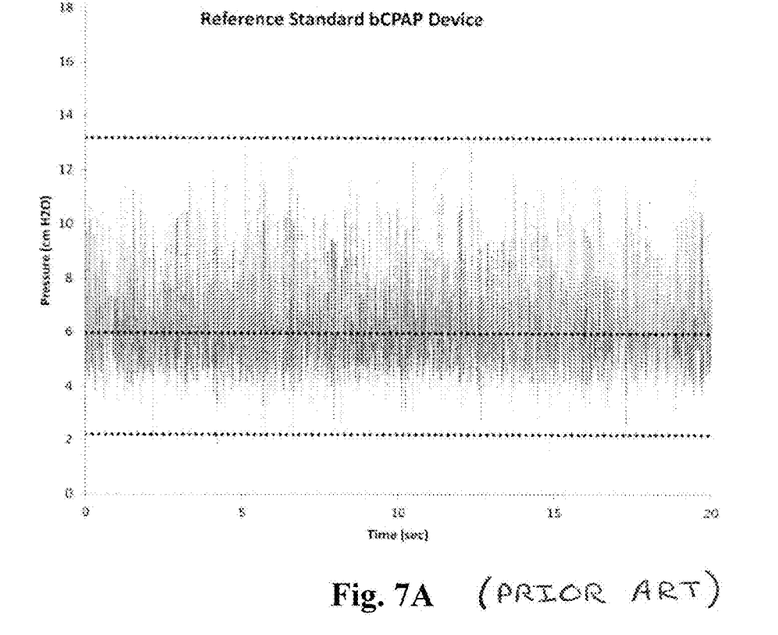
FIGS. 7A and 7B are two graphs displaying pressure vs. time at the nasal prongs for two bCPAP devices.
Figure 7B:
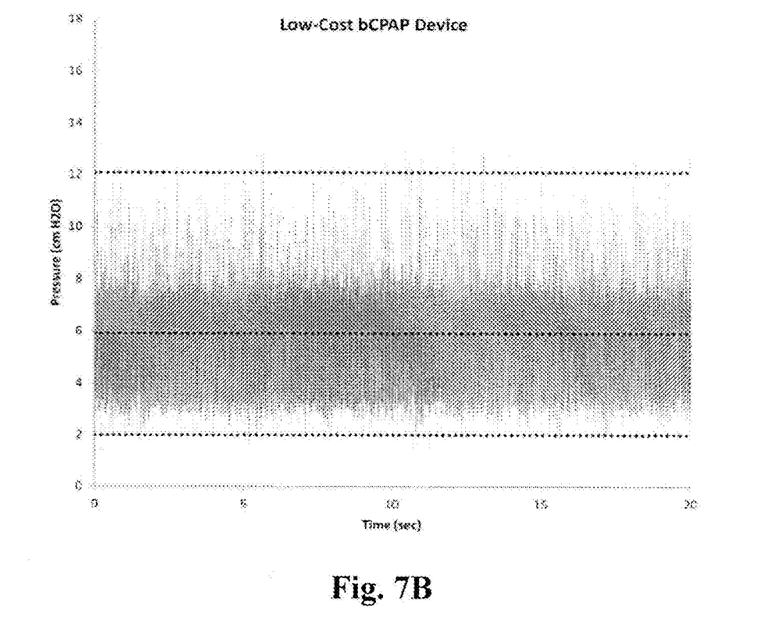

Table 3 below provides the operating specifications of the low-cost bubble CPAP device; the cost-of-goods to fabricate a single device at low production volume is approximately $350. FIG. 7 compares the nasal prong pressure vs. time for the low-cost bCPAP device and the reference standard bCPAP device at a flow rate of 7 L/min with the pressure control tube submerged in 6 cm of $H_2O$; the high frequency oscillations in pressure are associated with bubble formation at the distal tip of the pressure control tube. At these settings, both devices exhibit similar pressure waveforms, with an average pressure of 5.9 cm $H_2O$, and average minimum and maximum peak pressures of 2.7 and 12.1 cm $H_2O$ for the low-cost bCPAP device, and an average pressure of 6.0 cm $H_2O$, and average peak pressures of 3.3 and 13.2 cm $H_2O$ for the reference standard bCPAP device.

TABLE 3 bCPAP device operating specifications.

| Parameter | Specification |
| --- | --- |
| Size | 40 cm × 32 cm × 18 cm |
| Weight | 1.5 kg |
| Pressure | 0-8 cm $H_2O$ |
| Flow | 0-10 L/min |
| Air/Oxygen Mix | 40-60% Oxygen |

Figure 8:
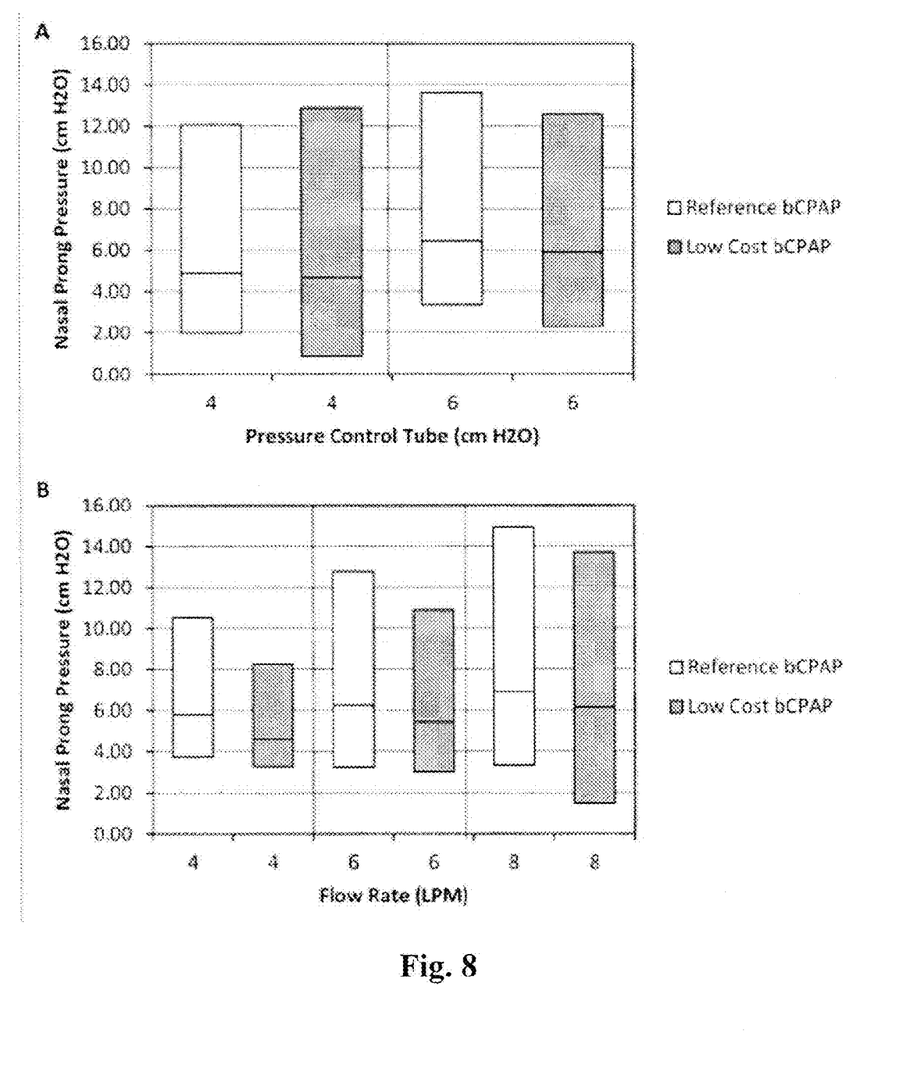
FIG. 8 is a comparison of reference standard and low-cost bCPAP output pressure under different flow and pressure settings. Each bCPAP system was assembled and nasal prong pressure was measured for 60 seconds of operation and mean pressures were calculated; results were then averaged for 10 independent trials of each system. In panel A, the mean pressure (mid-point of bar) and peak low and high pressures are shown at a flow rate of 7 L/min at varying pressure settings. In panel B, the mean pressure (mid-point of bar) and peak low and high pressures are shown at a pressure of 6 cm $H_2O$ and varying flow rates.

FIG. 8 shows the average pressure and average peak pressures measured for both devices as the flow rate changes from 4 to 8 L/min and the distal tip of the pressure control tube is submerged in increasingly greater depths of $H_2O$. Results reported are averaged across 10 independent measurements for the low-cost bCPAP and the reference standard device. Again, the devices show similar results, indicating that the devices deliver similar therapeutic pressures across a wide range of input parameters. Student t-tests were performed to test whether differences in the pressure data at each flow and pressure setting were statistically significant. There was no significant difference between the pressures generated by the two devices (student t-test, $p<0.01$).

Figure 9A:
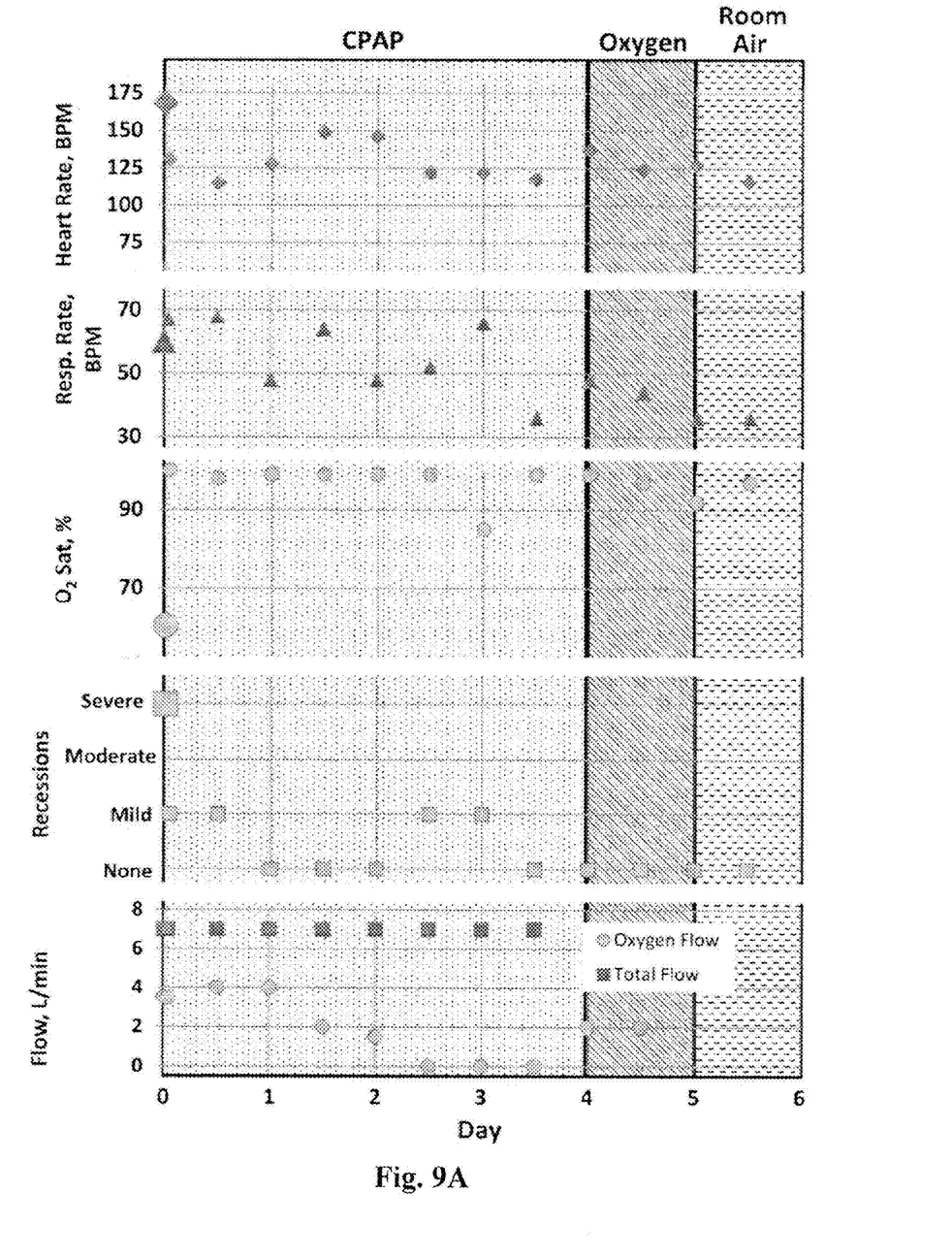
FIG. 9A is a graph displaying vital signs for 6-month old patient with bronchiolitis immediately before and after initiation of bCPAP. Time course immediately before treatment (large symbols) and after initiation of therapy (small symbols). The patient received CPAP treatment with gradually decreasing oxygen flow for 4 days, was then transitioned to nasal oxygen, and finally transitioned to room air. The patient was discharged on day 6.

The low-cost bCPAP device according to one embodiment of the present disclosure was used to treat a 6-month old baby admitted to Queen Elizabeth Central Hospital with bronchiolitis. Upon admission and immediately before undergoing bCPAP treatment, the child was unresponsive; her oxygen saturation was 60%, respiratory rate was 60 breaths per minute with severe recessions, and heart rate was 168 bpm. She was started on bCPAP therapy with a total flow rate of 7 L/min, 50% oxygen, and pressure of 6 cm $H_2O$; FIG. 9A tracks changes in the child's vital signs before initiation of bCPAP therapy and over time after initiation of bCPAP therapy. One hour after starting bCPAP therapy, her oxygen saturation was 100%, respiratory rate was 67 with mild recessions, and heart rate was 131 bpm. Within 6 hours of initiating bCPAP, she was able to breast feed. She remained on bCPAP for 4 days; during this time the flow rate was 7 L/min, but the fraction of oxygen was gradually decreased to room air after 3 days. No evidence of mucosal drying or other complications were observed during bCPAP treatment. After discontinuation of bCPAP therapy, she was placed on nasal oxygen (2 L/min) for 1 day. Oxygen therapy was discontinued on day 5, and she was discharged on day 6.

Figure 9B:
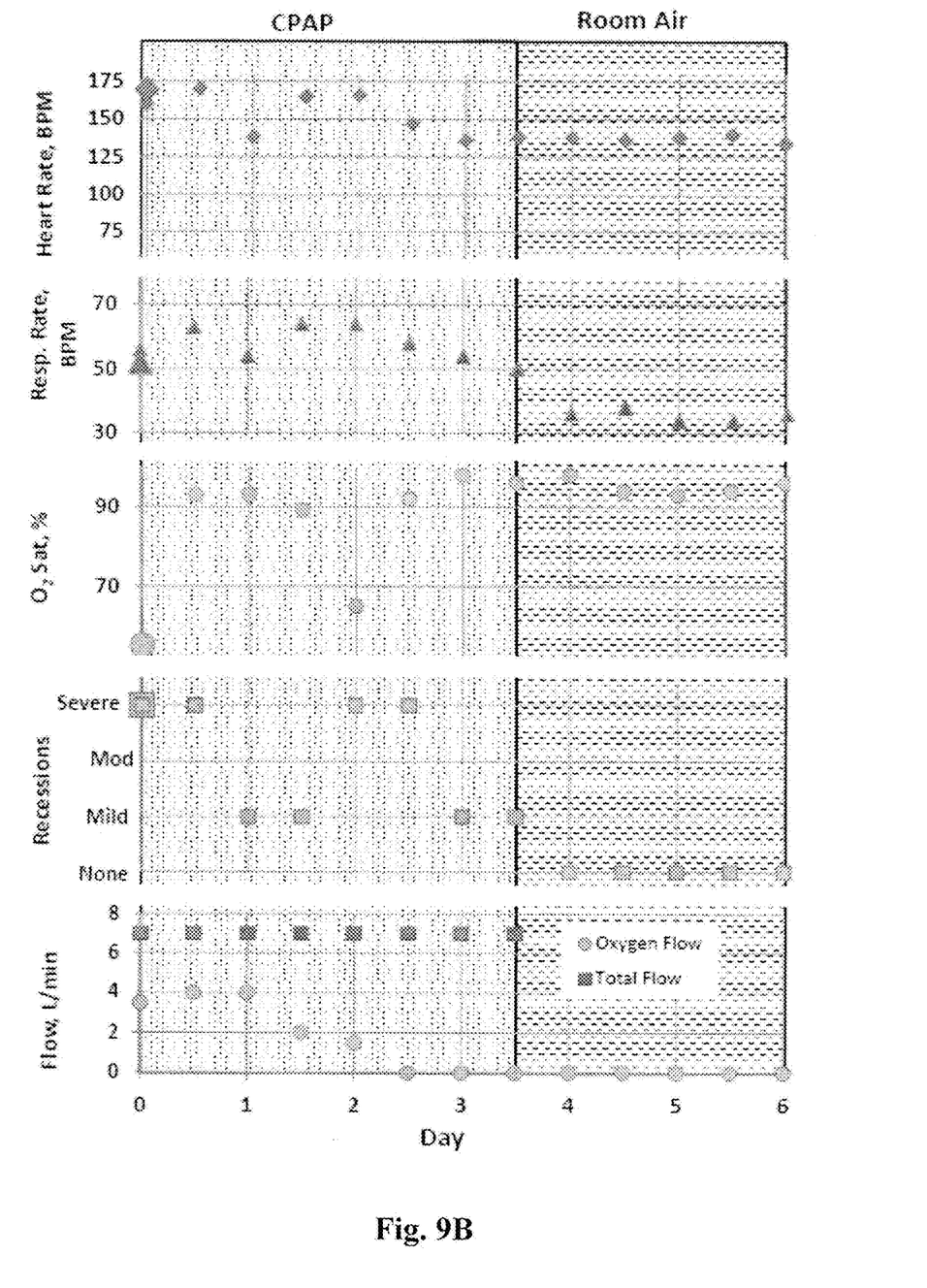
FIG. 9B is a graph displaying vital signs for a neonate with respiratory distress immediately before and after initiation of bCPAP. Time course immediately before treatment (large symbols) and after initiation of therapy (small symbols). The patient received CPAP treatment for 3.5 days. The fraction of oxygen was gradually decreased to room air during the first 2½ days.

The bCPAP device was also used to treat a full-term neonate with respiratory distress caused by congenital pneumonia. The baby's birth weight was 2.9 kg. His initial oxygen saturation was 55%, respiratory rate was 52 breaths per minute with severe recessions, and heart rate was 169 bpm. The baby was started on bCPAP therapy with a total flow rate of 7 L/min, 50% oxygen, and pressure of 6 cm $H_2O$; FIG. 9B tracks changes in the baby's vital signs before initiation of bCPAP therapy and over time after initiation of bCPAP therapy. Within 4 hours of initiating bCPAP, the baby's oxygen saturation was 93%, respiratory rate was 63 breaths per minute, and the heart rate was 170 bpm. He remained on bCPAP for 3.5 days; during this time the flow rate was 7 L/min, but the fraction of oxygen was gradually decreased to room air after 2½ days. No evidence of mucosal drying or other complications were observed during bCPAP treatment.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:

1. A method of administering bubble continuous positive airway pressure (bCPAP) to a patient, the method comprising:

connecting, via a bottle tube, a bottle tubing port of a bCPAP machine to a bottle containing liquid;

connecting, via a patient tube, a patient tubing port of the bCPAP machine to a patient interface;

inserting at least a portion of two prongs of the patient interface into nostrils of a patient to deliver pressured air from the bCPAP machine to the patient;
placing a hat on the patient, wherein the hat is formed by: cutting a stockinette based upon at least one measurement of the patient; twisting the stockinette; pulling one half of the stockinette over another half of the stockinette; and folding a bottom edge of the stockinette to form a brim; and
attaching at least a portion of the patient interface to the hat.

2. The method according to claim 1, further comprising:
connecting, via an oxygen tube, an oxygen port of the bCPAP machine to an oxygen source,
wherein a mixture of pressurized oxygen and air is delivered from the bCPAP machine to the patient.

3. The method according to claim 2, further comprising:
selecting a setting of any oxygen flow meter prior to selecting a setting of a total flow meter.

4. The method according to claim 1, further comprising:
placing the bottle into a bottle holder of the bCPAP machine; and
choosing an appropriate prong size for a patient interface based upon a characteristic of the patient.

* * * * *